United States Patent [19]

Schulte

[11] Patent Number: 4,497,824
[45] Date of Patent: Feb. 5, 1985

[54] METHOD OF CHEMICALLY DEBRIDING ULCERATED NECROTIC TISSUE

[76] Inventor: Thomas L. Schulte, 218 Family Farm Dr., Woodside, Calif. 94062

[21] Appl. No.: 571,417

[22] Filed: Jan. 17, 1984

Related U.S. Application Data

[63] Continuation-in-part of Ser. No. 456,896, Jan. 10, 1983, which is a continuation-in-part of Ser. No. 276,566, Jun. 23, 1981, Pat. No. 4,369,190.

[51] Int. Cl.³ .................. A61K 31/10; A61K 31/235
[52] U.S. Cl. .................................. 514/166; 514/947
[58] Field of Search ............................. 424/308, 337

[56] References Cited

U.S. PATENT DOCUMENTS 3,551,554  8/1968  Herschler ........................ 424/337
4,073,897  2/1978  Karlor ............................ 424/230

Primary Examiner—Stanley J. Friedman
Attorney, Agent, or Firm—Millen & White

[57] ABSTRACT

Debridement of ulcerated necrotic tissue of the skin or mucous membrane is promoted by aqueous solutions of biphenamine, optionally in admixture with a skin penetrant such as DMSO, thereby promoting healing of the lesion.

9 Claims, No Drawings

METHOD OF CHEMICALLY DEBRIDING ULCERATED NECROTIC TISSUE

This is a continuation-in-part of application Ser. No. 456,896, filed Jan. 10, 1983 as a continuation-in-part of application Ser. No. 276,566, filed June 23, 1981, now U.S. Pat. No. 4,369,190.

BACKGROUND OF THE INVENTION

This invention relates to a method for chemically debriding abnormal damaged or necrotic tissue.

The treatment topically of traumatized or pathological areas of the body having abnormal ischemic tissue around or covering a lesion is often hampered by the fact that the ischemic tissue presented by the affected area provides pathological surface presented by the affected area provides an effective barrier to natural healing process or the healing agent employed from normal tissue to thereby initiate the healing process. In such cases, physicians sometimes resort to the very painful task of manually debriding the abnormal tissue or covering the area with bandages soaked in medication to prevent infection while keeping the surface moist. Both of these approaches have obvious limitations and pose well-known problems. There therefore is a long standing need for an effective chemical debriding agent. There is also a need for a non-toxic, nonallergenic bacteriostat and fungistat which is also effective in promoting the normal healing of traumatized or pathological epithelium by suppressing infection and/or the natural inflammatory process.

The compositions of this invention comprise biphenamine (β-diethylaminoethyl 3-phenyl-2-hydroxybenzoate) base or pharmaceutically acceptable acid addition salt thereof. Salts of this compound are known to have a variety of activities, including local anesthetic (U.S. Pat. No. 1,976,922); treatment of seborrhea capitis in a shampoo (U.S. Pat. No. 3,123,531); as well as antihistaminic and bactericidal activity and fungicidal properties (U.S. Pat. No. 2,594,350; Report Annual Meeting So. Med. Assoc., Nov. 6, 1961).

Biphenamine hydrochloride has been sold as a 1% ointment, under the trademark "Melsaphine," as a topical anesthetic agent possessing bactericidal, fungicidal and antihistamine properties and as a 1% aqueous shampoo under the trademark "Alvinine," Federal Register, Vol. 34, No. 189, page 153, Oct. 2, 1969. See also U.S. Pat. No. 3,123,531.

Although its use in a shampoo for treating seborrhea and related conditions is claimed in U.S. Pat. No. 3,123,531, nothing was known concerning its ability to promote the healing of traumatized or pathological epithelium.

The topical compositions employed in the method of this invention preferably comprise, when the lesion is epithelial, an amount of a skin penetrant, e.g., DMSO (dimethyl sulfoxide) or propylene glycol, which by itself has no debriding or wound healing enhancement effects, at least in the amount employed. U.S. Pat. Nos. 3,551,554 and 3,711,602 disclose that DMSO is effective as an agent for enhancing tissue penetration of physiologically active agents. U.S. Pat. No. 3,549,770 discloses (Example 36) the topical application of a mixture of acetylsalicylic acid and DMSO is more effective than DMSO alone to relieve the pain and muscle spasm of rheumatoid spondylitis. See also U.S. Pat. Nos. 3,711,602; 3,711,606; and 3,743,727 and references cited therein. These patents disclose that the tissue penetration of physiologically active compounds, inter alia, steroidal agents and certain antimicrobial agents, can be enhanced by DMSO. U.S. Pat. No. 3,740,420 discloses DMSO compositions for topical administration containing thickening agents.

The foregoing patents disclose that concentrations of DMSO of 10% by weight and above can effect penetration of such agents through various mucous membrane barriers and that concentrations of 50% by weight and above are effective to achieve penetration thereof through the skin. DMSO is also known to enhance the antperspirant activity astringent of aluminum, zinc and zirconium salts (U.S. Pat. No. 3,499,961).

DMSO has been disclosed as useful for treating a variety of pathological conditions. U.S. Pat. No. 3,549,770 discloses topical application as a particularly advantageous route. This patent claims methods of relieving the signs and symptoms of tissue inflammation; of vascular insufficiency in the blood and lymph circulatory system; of respiratory distress; of arthritis and a method of promoting tissue repair, by administering an effective amount of DMSO, preferably topically. Dosages as low as 0.01 g/kg and up to 1.0 g/kg per day and sometimes higher dosages are contemplated with 0.1–0.2 g/kg individual doses being average. Higher concentrations of DMSO, such as at least 25% and more often at least about 50% are preferred for topical application. Treatment of pain with such solutions of DMSO, preferably by direct application to the involved area, is expressly contemplated. In one example (Example 27) the pain associated with skin abrasion was relieved with 15% DMSO in isotonic saline. 10% to 90% water solutions of DMSO, preferably 20% to 40%, in water, alcohol or glycerine are useful for topical application to the mucous membranes of the body although ". . . lower concentrations of DMSO say down to 3% by weight may be useful in some instances."

The use of DMSO as an ataratic agent is disclosed in U.S. Pat. No. 3,790,682. Pharmaceutical compositions containing DMSO and thickening agents are disclosed in U.S. Pat. No. 3,740,420, along with their use to treat and repair damaged tissue, as an anti-inflammatory agent, as an analgesic agent, as a muscle relaxant, as an agent for treating vascular insufficiency, and relieve the signs and symptoms of certain specific syndromes, viz., respiratory distress, arthritis and burns. None of the foregoing references disclose or suggest that chemical debriding can be achieved with low concentration of DMSO, e.g., topically on the skin at concentrations below 10%, although U.S. Pat. No. 3,549,770 discloses (Col. 10, lines 42–49) that for pharyngitis or hiccups, the subject may gargle with a more dilute aqueous solution, e.g., containing 1% or preferably 10% by weight of DMSO, and (Col. 28, lines 44–56) that concentrations of DMSO down to 3% by weight may be useful in some instances, with 10% to 90% water solutions being particularly suitable. The use of DMSO topically to promote the healing of traumatized or pathological epithelium at concentrations below 10% by weight is not suggested in the prior art. Moreover, I have found that low concentrations of DMSO or propylene glycol alone have little if any healing effect topically upon traumatized or pathological epithelium.

SUMMARY OF THE INVENTION

In a method of use aspect, this invention relates to a method for chemically debriding ulcerated necrotic tissue which comprises applying topically to the affected area an amount of biphenamine in an aqueous pharmaceutically acceptable carrier, effective to debride said tissue, thereby promoting the healing of the affected area. When the ulcer is epithelial, the biphenamine is preferably applied as an aqueous mixture with a water soluble topically acceptable ski penetrant.

DETAILED DISCUSSION

The aqueous mixture of biphenamine (base or acid addition salt thereof) and optional skin penetrant are applied topically to the ulcerated area of the skin or mucous membrane, e.g., of the mouth, throat, nasal passages, ear canals and drums, anal or vaginal regions, bladder or urethra. It is applied as a mixture in a pharmaceutically acceptable carrier or diluent, preferably aqueous. The mixture preferably is liquid, e.g., in the form of clear colutions, such as drops, aerosols or sprays, or in the form of lotions or other viscous aqueous liquids. The mixture can also be semi-solid or solid, e.g., in the form of an ointment or creas. Viscosity regulating agents, such as thickeners and gelling agents, e.g., glycerin, sodium carboxymethyl-cellulose, etc., can also be used to regulate flowability. See U.S. Pat. Nos. 3,740,420 and 3,711,602, whose disclosures are incorporated herein by reference. Propylene glycol itself is useful as a viscosity raising agent. They can be in the form of an oil-in-water or water-in-oil emulsion, as disclosed in U.S. Pat. No. 3,740,420, or as a single phase aqueous solution, the latter being preferred. Organic solvents, e.g., ethanol or isopropanol, can also be present.

The skin penetrant generally is present in the mixture at relatively low concentrations, e.g., at least about 1%, which concentrations lack any significant debriding activity in the absence of the biphenamine. DMSO is employed at concentrations of less than 10%, e.g., 3–7%, preferably about 5%. At these concentrations, DMSO exhibits neither the debriding and healing effects achieved when it is applied to the skin in admixture with biphenamine nor the side effects observed at higher concentrations, e.g., skin rash. Propylene glycol is employed at concentrations of about 1% to 90%, preferably about 5% to 15%, more preferably about 10%. Propylene glycol has desirable emollient and thickening qualities, which therefore makes it preferably in some formulations and with some patients.

Although the biphenamine can be present in the mixture employed at any convenient concentration, generally concentrations of up to 1% by weight, e.g., from about 0.1% to 1%, are employed except for instillations, where lower concentrations of about 0.001 to 0.01% should be employed. It preferably is present in the form of a pharmaceutically acceptable salt thereof, e.g., hydrochloride, hydrobromide, sulfate, phosphate, acetate, succinate, tartrate, benzoate, citrate, lactate or maleate, preferably the hydrochloride. Although acid addition salts of biphenamine are disclosed in U.S. Pat. No. 1,976,922 as having local anesthetic activity at a 2% concentration, neither its ability to promote healing when applied topically nor its effectiveness on the skin for any purpose at lower concentrations is suggested.

The biphenamine and optional skin penetrant are applied topically on successive occasions, e.g., as frequently as every hour or as infrequently as daily or longer, depending on the severity and intractibility of the pathological condition. In the case of severe burns, which produce ulcerated areas of the skin, it is desirable to apply the mixture promptly after the burn occurs and on successive occasions thereafter, e.g., once every 2–12 hours for 2–14 days or until the burn is healed.

The amount of the mixture applied to the affected area will depend on such factors as the degree of localization thereof, the concentration of biphenamine and skin penetrant therein and the individual's responsiveness to the therapy. As little as two or three drops per application may be effective as much as a fluid ounce may be required to cover the affected area. The effectiveness of successively greater or smaller dosages can determine the optimum effective individual dose. The mixture can be applied to small areas with an eyedropper or a piece of cotton and to larger areas as a spray or aerosol or with a surgically gloved hand.

The compositions of this invention are also effective for the amelioration of the pain associated with the condition being treated. From clinical observations, when a composition of this invention is applied to the affected area promptly after a skin burn and on successive occasions thereafter, not only is pain promptly ameliorated or eliminated, the healing process is facilitated, apparently by the suppression of the inflammatory response and infection. The compositions of this invention are also useful for promoting the heating of a variety of pathological conditions of the skin, and other topically accessible areas of the body, e.g., those caused by viral, bacterial, fungal and other microorganism infections or by localized inflammatory conditions, particularly those which produce a lesion in or a pathological thickening of the epithelium, e.g., scabs, tumorous tissue, e.g., herpes virus lesions, fungus infections of the perineum, feet, hands, ear canal, inflammation or sclerosis of the ear drum, urinary bladder, urethra, abscess cavities, leg ulcers, bed sores, infected sinuses, senile keratosis, animal and insect bits.

It is postulated on the basis of studies at the cellular level that enzyme imbalances cause physiological abnormalities which are corrected according to this invention by the skin penetrant carrying the biphenamine to the situs of the abnormality. Consequently, in addition to ameliorating the pain associated with wounds and burns, the healing thereof is facilitated by the compositions of this invention by the suppression of the inflammatory response. Additionally, the biphenamine inhibits infection of the situs of the wound and debriding of dead or injured tissue.

Although biphenamine hydrochloride as a 1% ointment is known to be useful for the treatment of minor burns, minor skin irritations or insect bites and to have bactericidal, fungicidal and antihistiminic properties at that concentration, it is surprising that concentrations thereof of only about 0.1% are equally or more effective when employed as an aqueous mixture with a skin penetrant such as DMSO or propylene glycol. Although U.S. Pat. No. 2,594,350 teaches that a 0.14% solution of the mandelic acid salt of biphenamine is useful as a urinary antiseptic and germicide, the activity thereof is due in part to the known urinary bactericidal activity of mandelic acid.

Contemplated equivalents of the method of this invention are methods otherwise corresponding thereto in which the affected area is a non-epithelial area with a lesion which is not covered by thickened or horny tissue and therefore does not require a skin penetrant to effectively debride the pathological tissue associated with the lesion.

The method of this invention can be employed to treat lesions associated with the following conditions, using biphenamine, preferably 0.1%, alone or in combination with a skin penetrant, e.g., DMSO, preferably at about 5% concentration:

debridng infected or traumatic wounds, thermal, electrical, chemical and traumatic burns; scrapes, abrasions; lesions associated with herpes of the urogenital tract; herpes intercostal, herpes labialis, herpes of the tongue, herpes on the inside of the mouth of gingiva, herpes of the face eye, nose, sinus, or occiput, and herpes of any nerve route; fungal infections which produce lesions; athlete's foot which produce fissures or lesions in the skin; plantar warts; varicose ulcers; leg ulcers from impaired circulation; hemorrhoids and fissures in the colon; sunburn; oral surgery, pimples, pustules or infected areas such as splinters or other bodies; insect bites; bladder inflammations; senile keratosis; skin cancers (basal cell or squamous epithelioma); human and animal bites; adenocarcinoma corpus uteri; adenocarcinoma large bowel; and any other necrotic wound to debride, whether benign or malignant, sterile or infected with bacteria virus or fungus.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The following are examples of compositions which can be employed in the method of this invention, which compositions are claimed in the above-cited parent application and patent.

COMPOSITION 1 a. An aqueous solution of DMSO and biphenamine hydrochloride can be produced by dissolving 50 grams of the former and 1 gram of the latter in 950 cc of sterile isotonic water. The viscosity thereof can be increased with any conventional viscosity enhancing agent, e.g., carboxymethylcellulose.

b. A solution of propylene glycol and biphenamine hydrochloride can be prepared by mixing 10 grams of the former with 900 grams of sterile water containing 1 gram of the latter dissolved therein. The propylene glycol acts as a viscosity enhancing agent, producing a viscous solution.

COMPOSITION 2 a. A lotion can be formulated in the conventional manner from the following ingredients, after dissolving the biphenamine hydrochloride and buffer in the water.
Biphenamine.HCL: 1 gm
DMSO: 50 cc
Cetyl alcohol: 200 gm
Propylene glycol: 100 gm
Sodium laural sulfate: 15 gm
Water q.s. 1000 cc.

b. The above lotion can also be prepared with the DMSO omitted therefrom.

COMPOSITION 3 a. An ointment can be produced from the following ingredients, after dissolution of the biphenamine hydrochloride in water.
Biphenamine.HCL: 1 gm
DMSO: 50 cc
Glyceryl monostearate, Acid Type 180 gm
Stearyl alcohol: 50 gm
Polysorbate 80: 20 gm
Water q.s. 1,000 cc.

b. An ointment can also be prepared in which the DMSO is replaced by 50 grams of propylene glycol.

COMPOSITION 4 a. An aqueous alcoholic ointment can be prepared by blending the following ingredients, with the biphenamine hydrochloride first dissolved in the water.
Biphenamine.HCL: 100 mg
DMSO: 5 gm
Ethanol: 10 gm
Corbowax 1,500: 20 gm
Water q.s. 1,000.

b. An ointment in which the DMSO is replaced by 10 gm of propylene glycol can similarly be prepared.

COMPOSITION 5 a. Suppositories can be cast from a melt of the following ingredients, after first dissolving the biphenamine hydrochloride in the water.
Biphenamine.HCL: 70 mg
DMSO: 3.4 gm
Sodium stearate: 10 gm
Glycerin: 45 gm
Water: 10 gm.

b. Suppositories in which the DMSO is replaced by 7 gm of propylene glycol can also be produced.

In each of the foregoing compositions, the DMSO can be omitted.

The following examples illustrate the use of compositions of this invention to promote the healing of wounds and burns and to ameliorate the pain associated therewith.

EXAMPLE 1

A construction worker received a ragged cut from a saw which was approximately two cm. long and about one cm. deep on the medial portion of the left hand. The would bled profusely and was very painful. First aid was instituted and the bleeding was stopped. The wound was disinfected and a tetanus shot administered. The wound was very painful for several days. Aqueous propylene glycol (10%) was applied to keep the wound pliable but there was no improvement and the pain persisted. Then a solution of Composition 1b was applied and relief of pain, which was observed within approximately 20 minutes, persisted for 4 hours. The same solution was again applied and was used over the course of the healing with application about every 4 hours. The wound healed without any further complications or further pain.

EXAMPLE 2

A female (72) patient developed acitinic keratitis, which corresponds to senile keratosis and is a precursor to squamous epithelioma. A dermatologist diagnosed and treated the condition with 5-flurouracil topically, which produced an intensely inflamed area with redness and pain. After the treatment was completed, an inflamed red area remained which was painful, swollen and unsightly. The application of the solution of Composition 1a resulted in immediate relief of pain. After several days the lesion disappeared and the skin appeared normal. Pain did not reoccur since the first application.

EXAMPLE 3

A female (72) spilled hot grease over the back of the left hand. Pain was severe. Immediately (2 min.) after the burn, the solution of Composition 1a was applied to the burn area. Pain disappeared in 3-5 minutes and never recurred. Twelve hours later, no blister had appeared. The solution was again applied to the burn area. The epithelial skin was darkened by the burn but there was neither blistering nor pain. The solution was applied 2-3 times daily for 7 days. On the 7th day, the dead epithelium flaked off leaving slightly pinker than normal skin underneath. In 10 days, the burned area was normal. There never was any pain, blister, cracking of the tissues or exudation of tissue fluid. Slight pigmentation was the only residual effect of the burn.

EXAMPLE 4

A male (73) was burned by the sharp corner of a red hot iron door of a Finnish Sauna over left ajar, which branded the lateral mid-thigh on the left side. There was the odor of burnt flesh and intense pain. The solution of Composition 1a was applied topically to the burned area within 1 minute of the burn and spread around the area. Within 3 minutes, there was no further pain. The solution was applied again several times over the next hour. After 12 hours, there still was no pain. No blister appeared but there was an obvious brand where the hot iron had penetrated the tissue. Further applications of the solution were made on 2 or 3 occasions the day of the burn and the day following, although they did not seem necessary because of the lack of pain. However, because the branding was so severe, the treatment was repeated, although there never was any further pain or blistering. The only evidence of the burn was a brand the shape of a V, where the corner of the red hot door made pressure contact with the tissue, and a wedge-shaped area below the branded area which appeared to be similar to the ecchymosis following trauma. However, the difference was that in the case of ecchymosis of trauma there is a more diffuse and rounded appearance to the ecchymotic area. The brownish wedge shaped area on the dependent side of the brand was outlined sharply, as if cut out of a piece of paper or cloth with straight sides coming together to form a point. It is assumed that this discoloration was the result of the tissue damage caused by the brand and the tissue fluids which diffused by gravity dependently. Presumably because of the immediate application of the solution of Composition 1a, there was no diffuse area of tissue damage surrounding the brand. After 10 days, the burn was healed and the brownish discoloration proximate the branded area returned to its normal color, except a slightly bluish hue.

EXAMPLE 5

A boy (6) fell from a horse, striking his face and head on the gravelled road. This resulted in a deepithelization of the skin and a traumatic burn into the subcutaneous tissues of the face and forehead. The body was in mild shock and severe pain but was able after some time to return home, which took 2 hours. Once home, the solution of Composition 1a was applied to the traumatized area by the child himself because he would not let anyone touch him. There was no cleaning or disinfection of the area because the child would not permit it. Instead, he applied the solution to himself liberally with cotton. In 20 minutes the boy fell asleep and awoke the next morning with swelling of the face and forehead but a minimal of pain. He permitted someone else to apply the solution again to the affected areas. Although these two applications were the only ones, there was no further pain and there was no infection that developed. After several weeks of healing, there was no scarring, pigmentation or other abnormality.

EXAMPLE 6

A male (23) playing soccer fell while running and skidded on the dry ground on his thigh, resulting in a burn that took off the skin and exposed a raw bleeding area. After a shower and soap and water (about 1 hour after the injury), the solution of Composition 1a was applied to the traumatized area. There first was a slight burning sensation followed a few minutes thereafter by complete relief of pain. The solution was applied again later the same day and the following morning. This was the only treatment. There was normal healing, no infection, never any pain and after the usual pigmentation resulting from such a trauma, this disappeared after a few weeks without scarring or evidence of injury.

EXAMPLE 7

A male (23) polo player took a spill going at a speed of about 30 miles an hour and skidded on the turf landing on his shoulder, arm, forearm and side of the face and received severe burns. Following the game, a shower, soap and water and cleaning the affected areas, the solution of Composition 1a was applied to all the affected areas except the forearm, which was used as a control. The areas where the solution was applied resulted in relief of pain in a few minutes hereas the area untreated on the forearm continued to be painful and did not heal as quickly as the areas where the solution had been applied.

The following examples illustrate the healing promoting effect of the compositions of this invention.

EXAMPLE 8

Several species of animals, viz., horses, dogs and cats, had severe traumatic penetrating and secondarily infected wounds. Most were foul smelling. Some were burns due to ropes, cinches, straps or saddle sores and assorted causes. The topical use of the solution of Composition 1a was effective in all cases in debriding and cleaning the infected areas and promoted healing without leaving angry appearing granulation tissue.

EXAMPLE 9

A female (72) with a mosquito bite on the base of the right thumb was treated with the solution of Composition 1a. Relief of itching was observed but a spread of the noxious material from the bite occurred and there was a continuation of the itching to a minor degree. On the following day a similar bite on the other thumb in the same place was treated with the solution of Composition 1b. The propylene glycol (10%) did not cause spread of the noxious material from the bite and there was a complete relief of itching which was much more marked than with the bite treated on the other thumb.

EXAMPLE 10

A female (70) with dermatitis of unknown etiology on the upper outer leg with raised areas that itched considerably was treated with a solution of Composition 1b which gave prompt relief of the itching and swelling.

EXAMPLE 11

A male (58) cut himself at the base of the left thumb with a chain saw. The area was extremely painful at the site of the cut and in the surrounding area. The application of the solution of Composition 1b relieved the pain, especially in the areas of trauma around the cut area. The following morning, there was very little pain and reapplication resulted in disappearance of all pain. There was prompt and complete healing without infection or residual soreness.

EXAMPLE 12

A pastured horse received a penetrating wound that became infected and fly blown with maggots falling out of the wound and the odor was bad enough so that none of the grooms would go near the horse. The wound was about six inches deep and about eight inches wide. The serum had exuded from the wound, as is the case in horses with an open wound that leaks serum, and tissue fluid and the hair inferior to the wound was missing due to the action of the tissue fluid exuding from the wound. The solution of Composition 1a was injected into the wound until it filled the wound and the excess ran out over the area that had been epilated. Within a few minutes the offensive odor was gone. The treatment was repeated daily, there was no odor, no maggots, no attraction to flies and the wound healed cleanly without leaving any granulation tissue that usually accompanies such a wound in the horse. The area where the hair was lost promptly grew back and the wound healed without leaving any ugly scar. The ability of the compositions of this invention to repel flying or jumping parasites has been noted in other instances.

EXAMPLE 13

A 3-year old female Laborador ran in front of an automobile, which braked and then ran over the left forefoot of the dog and dragged it along the gravel road for a distance of 20 feet, before stopping and backing off the dog's foot. The dog was immediately taken to a veterinarian who treated the dog and bandaged it tightly as well as treating with antibacterial medication. The following day there was a great amount of pain and swelling and the dog was taken to his regular veterinarian, who removed the pressure dressing and examined the damaged foot. The entire skin of the top, sides and bottom of the foot was missing. The pads on the bottom of the foot were also missing and there remained a raw swollen mass that was obviously quite painful and the dog whimpered whenever any part of the foot was touched. Thereafter, the only treatment was the solution of Composition 1a which was applied daily and a loose bandage was applied. The dog naturally walked on 3 legs for some time. After several days no bandage was used and the solution was applied from time to time but not at regular intervals. After a few weeks the dog's foot was normal.

Pain was relieved by the solution, as evidenced by the fact that the dog did not whimper when the loose bandage was applied or when the foot was touched when examined or when the solution was applied and rubbed on the area. There never was any infection and the area healed completely, including regrowth of the foot pads and the nails that had been lost.

The following examples illustrate the use of the comositions of this invention for the treatment of herpes lesions.

EXAMPLE 14

The topical application of the solution of Composition 1a to an 8-year old boy with anal herpes resulted in their disappearance. The condition recurred after a few months and a repeat of the topical application of the solution again resulted in a prompt disappearance of the perpetic lesions.

EXAMPLE 15

The solution of Composition 1a was applied to the lesions of a male (32) with genital herpes topically several times (3-4) a day. The lesions disappeared in a few days.

EXAMPLE 16

A male (59) with recurrent herpes labialis applied the solution of Composition 1a to the lesions as soon as a raised inflammed area appears. The lesion does not fully develop but instead disappears.

EXAMPLE 17

A male (44) developed severe intercostal herpes, possibly zoster. The topical application of the solution of Composition 1a resulted in a disappearance of the lesions.

EXAMPLE 18

A female (40) with herpes of the eye had a lesion in the internal canthus (inner corner of the eye). The lesion was a crusted lesion present for two days. The topical application of the solution of Composition 1a caused a prompt disappearance of the lesion.

EXAMPLE 19

A male (73) developed herpes of the inguinal nerve in the groin. The solution of Composition 1a was applied topically daily, which caused a rapid disappearance of the lesions. A pigmented area remained at the site but this also disappeared after several months.

The following examples illustrate the use of the solutions of this invention by instillation.

EXAMPLE 20

On the basis of animal experimentation and because of the established safety of the solution of Composition 1a by various routes of administration including orally, that solution was used to treat patients with interstitial cystitis. This is an extremely painful inflammatory condition of the urinary bladder which is thought to be an autoimmune disease and for which there is no cure. At times it is necessary to remove the bladder because of intractable pain. DMSO as a 50% solution is approved by the FDA for this condition.

A female (38) has a confirmed diagnosis of interstitial cystitis which was refractory to all treatment, including several courses of DMSO. Cortisone had also been administered intramurally (injected into the bladder wall) with only temporary benefit. Before considering cystectomy, it was decided to administer by local instillation topically the solution of Composition 1a. Despite the prior intractable nature of her condition, the patient was relieved of her pain for several weeks. Following a second local instillation, there was a relief of pain for a longer time. The intervals of relief of pain increased with each application of the solution. Although her condition was not cured, the topical local instillation was a definite benefit to the patient.

EXAMPLE 21

A female (58) with recurring hemorrhoids and rectal fissures with severe pain and itching was treated by the topical application of the solution of Composition 1a. Pain and itching were relieved promptly.

EXAMPLE 22

A male (65) with severe hemorrhoids and a severe fungus infection of the area of the anus and perineum was treated by topical application of the solution of Composition 1a. Pain and itching were relieved although the fungus infection had been present for many years and there was never any relief, in spite of frequent bathing and changing underwear twice or more daily.

EXAMPLE 23

A female (49) following a removal of the left kidney, developed a fecal fistula post operatively. The fecal material and flatus passed copiously from the sinus. Prior to considering surgical treatment, the wound was cleansed with the solution of Composition 1a. Surprisingly, not only was a debriding effect achieved and a clean wound obtained, the fistula healed and closed in 3 days.

EXAMPLE 24

A mare (12 years) with a severe uterine infection and a purulent discharge from the uterus had been treated with all known medications for infections by systemic and local administration including intrauterine packs of antibacterial drugs, in an attempt to clear up the infection prior to considering the possibility of getting her in foal. Her condition was noted by the farm manager, a veterinarian and several grooms, all of whom had seen and examined the mare previously on many occasions, including a speculum inspection of the cervix to determine her present condition. Thereafter, the solution of Composition 1a was installed into the mare's vagina on three successive occasions. Two weeks later, the mare was found to be clean and the infection which had been refractory to all other treatment was gone.

EXAMPLE 25

A female (44) with a severe infection of the cervix uteri refractory to other treatment took a vaginal douche using the solution of Composition 1a diluted with one tablespoonful of 1000 cc water. This was repeated once in 24 hours. After 2 weeks there was no evidence of infection or inflammation. This treatment was reported on several cases and always improved the patient's condition.

The following examples illustrate the use of the compositions of this invention for the treatment of respiratory and sinus inflammation and allergies.

EXAMPLE 26

A mare (3 years) had been roaring and bleeding on the race track as a result of the stress on racing. The solution of Composition 1a was sprayed into the nostrils once with complete relief of roaring and no bleeding as the result of racing. Thereafter, she won several races and was never ruled off the track because of bleeding. Several other race horses have been similarly treated.

EXAMPLE 27

A male groom (32) had severe allergies and would wake up in the morning with swollen eyes and puffy face. He applied the solution of Composition 1a directly into the nostrils at night before retiring. The following morning he awoke with none of the swelling of the eyes and face which he routinely suffered from. The treatment was repeated whenever necessary and was always effective.

Similar results were achieved in several other patients with similar allergy symptoms.

EXAMPLE 28

A man (63) had severe vertigo due to inflammation of the middle ear which did not respond to conventional treatment including several kinds of seasick pills. He placed the solution of Composition 1a in his external ear canal and a few hours thereafter used the solution, diluted one tablespoon to one ounce of water, as a gargle in the evening before retiring. The following morning the vertigo had disappeared.

EXAMPLE 29

A female (48) with symptoms similar to those of Example 28 was given the same treatment, with the exception tht she did not instill the medication in the external ear canal. The solution of Composition 1as was used as a gargle, diluted as before, one tablespoon (15 cc) in one ounce (30 cc) water. The following morning, there were no symptoms.

This gargle treatment has been used by many people for sore throat or with systemic flu-like symptoms with consistent benefit.

EXAMPLE 30

A female (68) with diagnosed epithelioma developing following senile keratosis in the same area of the right anterior mid leg was treated by radical surgical excision and skin graft to cover the area. Healing occurred in 6 months. A few months later a similar area developed on the opposite leg. This was treated with Composition 1a two to three times daily for several weeks. The result was complete return to normal appearing skin in the area. Two years later this area was still normal.

EXAMPLE 31

A male (83) had a history of multiple senile keratoses that were repeatedly cauterized by his physician. Following the application of Composition 1a, he was able to extend the time between such visits to his physician.

EXAMPLE 32

A male (65) with a history of many years of various treatments for senile keratoses, including "peeling off of the skin", since routine application to the affected area with Composition 1a has required no other form of treatment.

EXAMPLE 33

The repeated application of Composition 1a to the lesions of a female (75) with multiple recurrent senile keratoses resulted in a containment of the lesions without further treatment.

EXAMPLE 34

A male (56) with a senile keratosis of the back of the left hand had had several treatments of caustic chemicals and fulguration to the same lesion. He applied Composition 1a to the lesion for several weeks, which resulted in the disappearance of the lesion.

EXAMPLE 35

Wetting the foreleg hair of a horse carrying "bot" fly eggs with Composition 1a eliminated the infestation.

EXAMPLE 36

Daily moistening of the surface of both eyes of a human being wearing soft contact lens with a sterile 5.0% DMSO, 0.1% biphenamine hydrochloride solution permitted the person to wear the lenses without removing them for several weeks without the appearance of redness of irritation or build-up of proteinaceous opaque deposits on the lenses.

EXAMPLE 37

A man (60) with his right arm amputated at the elbow for a squamous cell epithelioma had a mass the size of a large cantaloupe at the amputation stump along with several infected sinuses that were draining a foul material. After two days of local irrigation with Composition 1a, there was a sluff of the necrotic material including one of the arteries that had to be clamped to control hemorrhage. The lesion became reduced in size to a normal stump with a resolution of the cancerous mass.

EXAMPLE 38

A woman (56) has a basal cell epithelioma of the right side of the face that represented itself as a fungating mass. The upper jaw was involved as was the maxilla, the right eye and the orbit was destroyed. A few drops of Composition 1a diluted 1/10 was applied and a few days later there appeared a sinus in the area of the maxilla. This sinus was instilled with the solution and within a few days the entire right side of the face sluffed away, leaving a clean hole projecting up under the cranium. There was no upper jaw, no sinuses, no orbit, no eye, but a perfectly clean wound with no infection and no bleeding. The patient could only eat liquid food. Accordingly, a high protein, vitamin and mineral mix was added to milk or fruit juice. She improved and 6 weeks later the wound was ready for plastic surgical closure.

EXAMPLE 39

A woman (54) had a grade II epithelial tumor. The lesion was a biopsy from the cervix uteri after a Pap smear was positive. After a few days of vaginal instillation of 10 cc of a 0.1% biphenamine hydrochloride, 5% DMSO aqueous solution daily, the patient noticed that her severe athlete's foot fungus infection of the toes and toe nails was improving. Since there was no local topical contact with the solution and the feet, it was postulated that a systemic absorption of the biphenamine from the vagina and cervix uteri occurred. (It has been demonstrated that a very dilute solution of biphenamine hydrochloride in tissue culture will protect cells against heat damage as compared to controls. Therefore, it is assumed that a very small amount absorbed systemically can be biologically effective.) A subsequent pap smear was negative, indicating debridement of surface necrotic cells since the tumor had not been otherwise treated.

EXAMPLE 40

Debridement of necrotic tissue associated with a scratched cornea or bacterial or viral infection, or parasitic infestation of the eye or associated hair follicles or tear duct, e.g., a stye or face fly eggs in the tear duct, or irritation from a foreign body between the eyeball and the lid, with associated supperation, is facilitated and promoted by washing the affected eye every 1-6 hours with a sterile 0.1% aqueous solution of biphenamine hydrochloride.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for promoting the healing of an abnormal, ulcerated necrotic tissue on skin or mucous membrane of a patient which comprises applying topically to the affected area of the patient an amount of biphenamine, as an aqueous mixture comprising a pharmaceutically acceptable carrier, effective to promote debridement of necrotic tissue from the affected area, thereby promoting the healing of the affected area.

2. A method according to claim 1 wherein the affected area is on the skin.

3. A method according to claim 2 wherein the mixture is applied to the affected area on successive occasions.

4. A method according to claim 1 wherein the biphenamine is applied as a mixture with a topically acceptable skin penetrant.

5. A method according to claim 1 wherein the skin penetrant is DMSO.

6. A method according to claim 5 wherein the biphenamine is present in the mixture as the hydrochloride salt thereof at a concentration of about 0.1% to 1% and DMSO is present therein at a concentration of about 3% to 7%.

7. A method according to claim 6 wherein the mixture is applied to the affected area at least once a day on a plurality of successive days.

8. A method according to claim 6 wherein the DMSO is present in the mixture at a concentration of about 5% and the biphenamine hydrochloride is present therein at a concentration of about 0.1%.

9. A method according to claim 8 wherein the affected area is the skin and the mixture is applied to the affected area at least once a day on a plurality of successive days.

* * * * *